United States Patent [19]

Gruber et al.

[11] Patent Number: 5,206,396
[45] Date of Patent: Apr. 27, 1993

[54] TELOMERIZATION OF 1,3-BUTADIENE

[75] Inventors: Bert Gruber, Bedburg, Fed. Rep. of Germany; Kenneth J. Weese, Santa Rosa; Steven M. Hoagland, San Francisco, both of Calif.; Hans-Peter Mueller, Neusse, Fed. Rep. of Germany; Karlheinz Hill, Santa Rosa, Calif.; Arno Behr, Benrath, Fed. Rep. of Germany; James R. Tucker, Cincinnati, Ohio

[73] Assignee: Henkel Research Corporation, Santa Rosa, Calif.

[21] Appl. No.: 558,047

[22] Filed: Jul. 25, 1990

[51] Int. Cl.$^5$ .................................................. C09F 7/06
[52] U.S. Cl. .................................... 554/27; 556/21; 560/233; 560/244; 568/651
[58] Field of Search ................. 260/410, 410.9 R; 568/651; 860/233, 244; 556/21; 554/27

[56] References Cited

U.S. PATENT DOCUMENTS

| | | | |
|---|---|---|---|
| 3,489,813 | 1/1970 | Dewhirst | 260/611 |
| 3,499,042 | 3/1970 | Smutny | 260/614 |
| 3,518,315 | 6/1970 | Smutny | 260/612 |
| 3,670,032 | 6/1972 | Romanelli | 260/614 AA |
| 3,746,749 | 7/1973 | Mitsuyasie et al. | 260/497 |
| 3,769,352 | 10/1973 | Romanelli | 260/614 AA |
| 3,792,101 | 2/1974 | Hattori et al. | 260/677 R |
| 3,887,627 | 6/1975 | Romanelli | 568/840 |
| 3,891,684 | 6/1975 | Jung | 260/429 R |
| 3,923,875 | 12/1975 | Rose et al. | 260/497 A |
| 3,992,456 | 11/1976 | Atkins et al. | 260/632 R |
| 4,006,192 | 2/1977 | Enomoto et al. | 260/615 R |
| 4,142,060 | 2/1979 | Kuntz | 568/840 |
| 4,146,738 | 3/1979 | Jadamus et al. | 568/690 |
| 4,196,135 | 4/1980 | Enomoto et al. | 260/429 R |
| 4,219,677 | 8/1980 | Kuntz | 568/657 R |
| 4,260,750 | 4/1981 | Kuntz | 544/178 |
| 4,356,333 | 10/1982 | Yoshimura et al. | 568/840 |
| 4,417,079 | 11/1983 | Yoshimura et al. | 568/903 |
| 4,454,333 | 6/1984 | Jenck | 560/1 |
| 4,515,711 | 5/1985 | Chalk et al. | 252/522 |
| 4,522,760 | 6/1985 | Jenck | 260/410.9 R |
| 4,642,392 | 2/1987 | Hanes | 568/690 |

FOREIGN PATENT DOCUMENTS

| | | |
|---|---|---|
| 2143071 | 3/1972 | Fed. Rep. of Germany . |
| 2154370 | 5/1973 | Fed. Rep. of Germany . |
| 2505180 | 8/1976 | Fed. Rep. of Germany . |
| 73042606 | 3/1967 | Japan . |
| 73003605 | 1/1968 | Japan . |
| 72020604 | 3/1968 | Japan . |
| 49031965 | 12/1969 | Japan . |
| 47031906 | 3/1971 | Japan . |
| 74046286 | 12/1971 | Japan . |
| 7246566 | 11/1972 | Japan . |
| 48-37007 | 11/1973 | Japan . |
| 49048613 | 5/1974 | Japan . |
| 7443932 | 11/1974 | Japan . |
| 49125313 | 11/1974 | Japan . |
| 75022530 | 7/1975 | Japan . |
| 50-34002 | 11/1975 | Japan . |
| 50-157301 | 12/1975 | Japan . |
| 51-008206 | 1/1976 | Japan . |
| 51-142532 | 12/1976 | Japan . |
| 51-149206 | 12/1976 | Japan . |
| 7704526 | 2/1977 | Japan . |
| 53-9701 | 1/1978 | Japan . |
| 57-007426 | 1/1982 | Japan . |
| 1248592 | 10/1971 | United Kingdom . |
| 1248593 | 10/1971 | United Kingdom . |
| 1354507 | 5/1974 | United Kingdom . |
| 2054394 | 2/1981 | United Kingdom . |
| 2114974 | 9/1983 | United Kingdom . |

OTHER PUBLICATIONS

Walker et al., Tetrahedron Letters, vol. 43, pp. 3817-3820, 1977.

(List continued on next page.)

Primary Examiner—Jose G. Dees
Assistant Examiner—D. D. Carr
Attorney, Agent, or Firm—Ernest G. Szoke; Wayne C. Jaeschke; John E. Drach

[57] ABSTRACT

Octyl ethers and octadienyl ethers of glucose, sucrose, bisphenol A, 4-substituted-2,2,6,6-tetramethylpiperidines are disclosed. Compositions comprised of a mixture of octyl ethers of glucose and sucrose and those containing octadienyl ethers of sugar acids and ring-opened epoxidized octadienyl ethers are also disclosed as are telomerization processes.

9 Claims, No Drawings

OTHER PUBLICATIONS

Jolly, "Organometallics" 4, 1945–53 (1985).
Bochmann, "J. Molec. Catalysis" 26, 79–88 (1984).
Dzhemilev, "Zh. Org. Khim." 22(8), 1591–7 (1986) (translation).
Behr, "Organometallics" 5, 514–8 (1986).
Jolly, "Organometallics" 5, 473–81 (1986).
Behr, "Aspects of Homogeneous Catalysis" 5, 5–58 (1984).
Groult, "Tetrahedron" 39, (9) 1543–50 (1983).
Teranishi, "J. Org. Chem." 46, 2356–62 (1981).
Dzhemilev, "Izv. Akad. Nauk, SSSR, Ser. Khim." 8, 1837–425 (1981) (translation).
Keim, "J. Molec. Catalysis" 10, 247–252 (1981).
Dzhemilev, "Zh. Org. Khim," 16 (6), 1157–61 (1980) (translation).
Yoshida, "Tetr. Letters" 21, 3787–90 (1980).
Tsuji, "Pure & Appl. Chem." 51, 1235–41 (1979).
Tsuji, "Adv. in Organometallic Chem." 17, 141–93 (1979) (not available).
Baker, "Chemical Reviews" 73 (5), 503–9 (1973).
Tsuji, "Accounts Chem. Res." 6 (1), 8–15 (1973).
Smutny, "Annals N.Y. Acad. Sci." 214, 124–142 (1973).
Rose, "J. Organometallic Chem." 49, 473–6 (1973).
Smutny, "ACS, Div. Petr. Chem.", Prepn. 14 (2), B100–11 (1969).
Takahashi, "Bull. Chem. Soc. Japan" 41, 254–5 (1968).
Takahashi, "Bull. Chem. Soc. Japan" 41, 454–60 (1968).
Smutny, "J. Am. Chem. Soc." 89, 6793–4 (1967).
Takahashi, "Tetr. Letters" (26), 2451–3 (1967).
"Zh. Org. Khim." 19(2), 463 (1983) (CA 98: 215363e).

TELOMERIZATION OF 1,3-BUTADIENE

BACKGROUND OF THE INVENTION

1. Field of the Invention

This invention relates to new octyl ethers and octadienyl ethers.

2. Statement of Related Art

It is known in the art that conjugated dienes can telomerize with alcohols to give 1,7-and 2,7-alkadienyl ethers. The following references exemplify extensive patent and other literature that relate to such telomerization reactions and novel compounds prepared by such reactions: U.S. Pat. Nos. 3,489,813; 3,499,042; 3,670,032; 3,769,352; 3,792,101; 3,887,627; 3,891,684; 3,923,875; 3,992,456; 4,006,192; 4,142,060; 4,146,738; 4,196,135; 4,219,677; 4,260,750; 4,356,333; 4,417,079; 4,454,333; 4,515,711; 4,522,760; and 4,642,392. British Patent Nos. 1,248,592; 1,248,593; 1,354,507; 2,054,394; and 2,114,974. German Patent Nos. 1,807,491; 2,154,370; and 2,505,180. Japanese Patent Nos. 72,020,604; 47,031,906; 48,039,413; 73,042,606; 73,003,605; 49,031,965; 49,048,613; 49,125,313; 74,046,286; 50,157,301; 51,008,206; 51,142,532; 51,149,206; and 51,007,426. Literature articles: Behr, Organometallics 5,514-8 (1986) Jolly, Organometallics 5, 473-81 (1986) Dzhemilev, Zh. Org. Khim. 22 (8), 1591-7 (1986) Gaube, J. Prakt. Chim. 327 (4), 643-8 (1985) Jolly, Organometallics 4, 1945-53 (1985) Bochmann, J. Molec. Catalysis 26, 79-88 (1984) Behr, Aspects of Homogeneous Catalysis 5, 5-58 (1984) Gaube, J. Prakt. Chem. 326, (6) 947-54 (1984) Behr, Chem. Ber. 116, 862-73 (1983) Groult, Tetrahedron 39, (9) 1543-50 (1983) Teranishi, J. Org. Chem. 46, 2356-62 (1981) Dzhemilev, Izv. Akad. Nauk. SSSR, Ser. Khim. 8, 1837-425 (1981) Keim, J. Molec. Catalysis 10, 247-252 (1981) Dzhemilev, Zh. Org. Khim. 16 (6), 1157-61 (1980) Yoshida, Tetr. Letters 21, 3787-90 (1980) Tsuji, Pure & Appl. Chem. 51, 1235-41 (1979) Tsuji, Adv. in Organometallic Chem. 17, 141-93 (1979) Singer, J. Organomet. Chem. 137 (3), 309-14 (1977) Chauvin, Tet. Letters 51, 4559-62 (1975) Chauvin, Bull. Soc. Chim. Fr. 652-6 (1974) Beger, J. Prakt. Chem. 315 (6), 1067-89 (1973) Baker, Chemical Reviews 73 (5), 503-9 (1973) Tsuji, Accounts Chem. Res. 6 (1), 8-15 (1973) Smutny, Annals N.Y. Acad. Sci. 214, 124-142 (1973) Chauvin, Tetr. Letters 51, 4559-62 (1973) Rose, J. Organometallic Chem. 49, 473-6 (1973) Smutny, ACS, Div. Petr. Chem., Prepn. 14 (2), B100-11 (1969) Takahashi, Bull. Chem. Soc. Japan 41, 254-5 (1968) Takahashi, Bull. Chem. Soc. Japan 41, 454-60 (1968) Smutny, J. Am. Chem. Soc. 89, 6793-4 (1967) Takahashi, Tetr. Letters (26), 2451-3 (1967). Lactic and tartaric acids are included in a list of preferred carboxylic acids which can be used to make unsaturated esters of carboxylic acids by reacting the acids with a conjugated diene in the presence of a palladium catalyst in U.S. Pat. No. 3,746,749. The patent contains no teaching or disclosure of how to make any of the claimed alkadienyl esters and/or ethers of the present invention. A copending application Ser. No. 07/517,990 filed on May 2, 1990 teaches 1-and 3-substituted octadienyl esters and ethers of hydroxy-substituted carboxylic acids including 2,2-dimethylolpropionic acid. Japanese Patent 7704526 (CA 87:117573b) teaches the preparation of aminohydroxyoctyl ethers by reaction of diepoxy ethers with amines and alkanolamines. Japanese Patent 7443932 (CA 83:27612b) teaches the preparation of aminohydroxyoctyl fatty esters by aminolysis of 2,3;7,8-diepoxyoctyl fatty esters. U.S. Pat. No. 3,746,749 also teaches that alcohols can be used as solvents in the telomerization of conjugated dienes with carboxylic acids in conjunction with from 0.1 to 10 moles of an alkali metal salt of a carboxylic acid/mole of carboxylic acid. U.S. Pat. No. 3,923,875 teaches an improved process for producing alkadienol esters which comprises reacting a 1,3-conjugated acyclic diolefin wherein the improvement consists of conducting the process in the presence of a palladium or palladium (II) compound and a mononuclear triarylphosphite in which at least one of the aryl radicals is substituted in the ortho position in the absence of a reaction solvent. The patent also teaches that an inert solvent such as benzene, toluene, ethers, and esters can be used. There is no teaching of the use of alcohol solvents. Japanese patent JP 5034002 (CA 86:4946m) teaches the telomerization of 1,3-butadiene with carboxylic acids in the presence of aprotic solvents using palladium acetate. Japanese patent JP 75022530 teaches the telomerization of a conjugated diene with a carboxylic acid in the presence of palladium acetylacetonate/triphenylphosphine in the presence of unspecified polar solvents. Japanese patent JP 7246566 (CA 78:71465b) teaches the telomerization of 1,3-butadiene with carboxylic acids in the presence Pd(II)(Ph$_3$P)$_3$ and a solvent such as acetone, diethyl ether, ethyl acetate, THF, and DMF.

Zh. Org. Khim. 19(2), 463 (1983) (CA 98:215363e) teaches the epoxidation of a 2,7-octadienyl ester of acetic acid by t-butyl hydroperoxidemolybdenum hexacarbonyl in benzene at 80° C. to give the corresponding monoepoxide. Japanese Kokai 53/9701 (CA 88:169938q) teaches the epoxidation of a 2,7-octadienyl ester of terephthalic acid with peracetic acid. Japanese patent JP 4837007 (CA 81:78466y) also teaches the epoxidation of a 2,7-octadienyl ester of terephthalic acid with peracetic acid. German patent DE 2143071 (CA 77:20675s) teaches the epoxidation of a 2,7-octadienyl ester of tetrahydrophthalic acid with peracetic acid.

The use of low levels of palladium catalyst in 1,3-butadiene telomerizations is disclosed in British patent No. 2,114,974. This patent teaches that when 1,4-butanediol, 1,5-pentanediol, and 1,6-hexanediol telomerized with butadiene, about a 61% yield of monoether based on butadiene can be realized by using a molar ratio of catalyst/diene equal to about 1/20,600. The patent also discloses that a large stoichiometric excess of diol is also necessary in order to obtain high yields of the desired monoether product. For best yields of monoether, the above patent also teaches that the optimum catalytic effect is obtained by combining the palladium catalyst with a nickel(II) compound and a base such as a quaternary ammonium hydroxide. The patent also discloses a method of removing the palladium catalyst with ion exchange resins from the reaction mixture after the reaction has been completed. The palladium levels are obviously not low enough to preclude the recovery step; an operation which the present invention eliminates. U.S. Pat. No. 3,746,749 discloses that octadienyl esters of adipic acid can be prepared in 86% yield by employing a molar ratio of Pd/Acid/Butadiene equal to 1/12,300/56,000 and octadienyl esters of fumaric acid can be prepared in 67% yield by employing a molar ratio of Pd/Acid/Butadiene equal to 1/60,000/28,000. However, these low palladium levels are used in conjunction with from 0.1 to 10 moles of an alkali metal salt of a carboxylic acid/mole of carboxylic acid. U.S. Pat. No. 3,518,315 teaches that 2,2-bis(4-(2,7-octadienyloxy)phenyl) propane is formed by the telomerization of 1,3-butadiene with 2,2-bis(4-hydroxyphenyl) propane (bisphenol A) using a palladium (II) catalyst wherein the palladium (II)/bisphenol A/butadiene ration is 1/39/295 at a temperature of 100° C. for 48 hours.

SUMMARY OF THE INVENTION

One aspect of the present invention relates to sucrose mono-octyl ether, sucrose di-octyl ether, sucrose tri-octyl ether, sucrose tetra-octyl ether, sucrose penta-octyl ether, sucrose hexa-octyl ether, sucrose hepta-octyl ether, and sucrose octa-octyl ether. Another aspect of the invention relates to a composition which comprises sucrose, sucrose mono-octyl ether, sucrose di-octyl ether, sucrose tri-octyl ether, sucrose tetra-octyl ether, sucrose penta-octyl ether, sucrose hexa-octyl ether, sucrose hepta-octyl ether, and sucrose octa-octyl ether. The individual sucrose ethers and the mixture of sucrose ethers are useful as surfactants and emulsifiers. Still another aspect of the invention relates to glucose di-octyl ether, glucose tri-octyl ether, glucose tetra-octyl ether, glucose penta-octyl ether. A further aspect of the invention relates to a composition which comprises glucose, glucose mono-octyl ether, glucose di-octyl ether, glucose tri-octyl ether, glucose tetra-octyl ether, and glucose penta-octyl ether. The individual glucose ethers and the mixture of glucose ethers are useful as surfactants and emulsifiers.

Yet another aspect of the invention relates to a process for the telomerization of 1,3-butadiene with bisphenol A which comprises reacting 1,3-butadiene with bisphenol A in the presence of a palladium (II) catalyst at a temperature of from about 70° C. to about 100° C. for a period of time from about 2 hours to about 12 hours wherein the palladium (II)/bisphenol A/diene molar ratio is from about 1/2500/4800 to about 1/60,000/300,000.

Still another aspect of the invention relates to octadienyl derivatives of substituted 2,2,6,6-tetramethylpiperidines of the formula III or IV useful as U.V. stabilizers

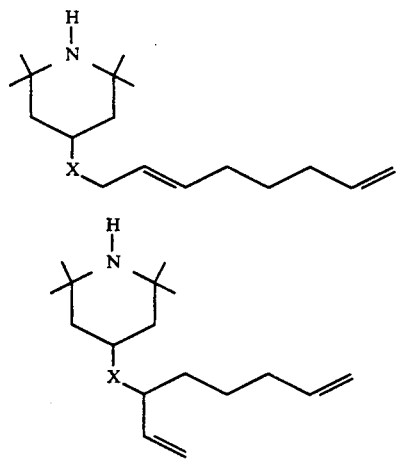

wherein X is O, NH, COO, or S.

A further aspect of the present invention relates to the product formed by the process of reacting a sugar acid of the formula V

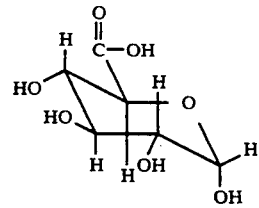

with 1,3-butadiene in the presence of a palladium (II) catalyst at a temperature of less than about 90° C.

Another aspect of the invention relates to a composition comprised of compounds of the formula VI, VII, VIII, IX, X, and XI

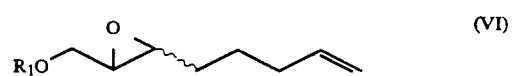

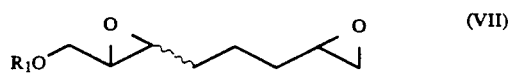

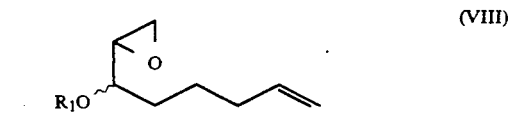

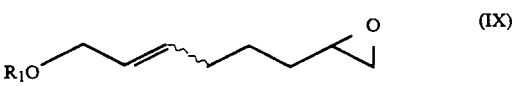

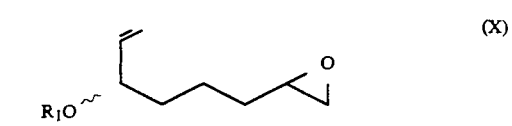

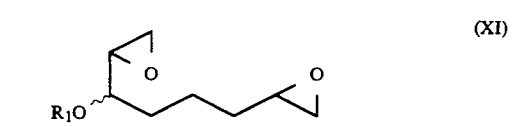

wherein $R_1$ is a $C_{1-25}$ alkyl radical; a benzenoid aromatic or substituted benzenoid radical; or an aliphatic or benzenoid aromatic acyl radical.

An additional aspect of the present invention relates to the product formed by the process comprising reacting a composition comprising a mixture of compounds of the formula VI, VII, VIII, IX, X, and IX,

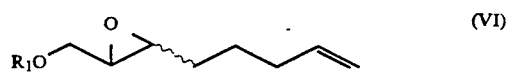

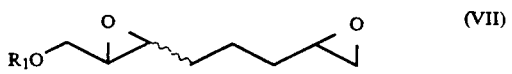

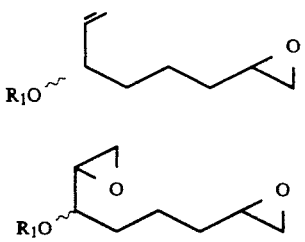

wherein $R_1$ is a $C_{1-25}$alkyl radical; a benzenoid aromatic or substituted benzenoid radical; or an aliphatic or benzenoid aromatic acyl radical with a compound selected from the group consisting of an aliphatic or aromatic alcohol, a primary aliphatic or aromatic amine, a secondary aliphatic or aromatic amine, HF, HCl, HBr, HI, water, HCN, $NaHSO_3$, and a Grignard Reagent.

A further aspect of the present relates to a process for telomerizing 1,3-butadiene with a carboxylic acid which comprises reacting 1,3-butadiene and a carboxylic acid in the presence of a catalyst effective amount of a palladium (II)/tris-(aryl)phosphite catalyst in the presence of a secondary or tertiary alcohol.

DESCRIPTION OF THE PREFERRED EMBODIMENTS

The octyl ethers of glucose according to the invention include glucose dioctyl ether, glucose tri-octyl ether, glucose tetra-octyl ether, glucose penta-octyl ether. The term glucose di-octyl ether includes any and all of the possible isomers wherein two of the five OH groups of glucose are etherified by a 1- or 3-octyl group. The term glucose tri-octyl ether includes any and all of the possible isomers wherein three of the five OH groups of glucose are etherified by a 1- or 3-octyl group. The term glucose tetra-octyl ether includes any and all of the possible isomers wherein four of the five OH groups of glucose are etherified by a 1- or 3-octyl group. The term glucose penta-octyl ether means that all five OH groups of glucose are etherified by a 1- or 3-octyl group. The composition which comprises glucose, glucose mono-octyl ether, glucose di-octyl ether, glucose tri-octyl ether, glucose tetra-octyl ether, and glucose penta-octyl ether includes any combination of the glucose ethers defined above as well as any and all of the possible isomers wherein one of the five OH groups of glucose is etherified by a 1- or 3-octyl group. The preferred amounts of the individual octyl ethers in the composition are from about 0% to about 20% glucose; from about 0% to about 20% glucose mono-octyl ether, from about 5% to about 50% glucose di-octyl ether, from about 10% to about 60% glucose tri-octyl ether, from about 0% to about 50% glucose tetra-octyl ether, and from about 0% to about 25% glucose penta-octyl ether. A particularly preferred embodiment is a composition comprising glucose di-octyl ether and glucose tri-octyl ether.

The glucose octyl ethers according to the invention can be made by any etherification method known to those skilled in the art such as reaction of a 1-octyl halide with a mono- or poly-alkoxide salt of glucose. The preferred method comprises preparing the octadienyl ethers of glucose by the method disclosed in co-pending patent application Ser. No. 07/517,990 filed on May 2, 1990 and then saturating them with hydrogen.

The octyl ethers of sucrose according to the invention include sucrose mono-octyl ether, sucrose di-octyl ether, sucrose tri-octyl ether, sucrose tetra-octyl ether, sucrose penta-octyl ether, sucrose hexa-octyl ether, sucrose hepta-octyl ether, and sucrose octa-octyl ether. The term sucrose mono-octyl ether includes any and all of the possible isomers wherein one of the eight OH groups of sucrose is etherified by a 1- or 3-octyl group. The term sucrose di-octyl ether includes any and all of the possible isomers wherein two of the eight OH groups of sucrose are etherified by a 1- or 3-octyl group. The term sucrose tri-octyl ether includes any and all of the possible isomers wherein three of the eight OH groups of sucrose are etherified by a 1- or 3-octyl group. The term sucrose tetra-octyl ether includes any and all of the possible isomers wherein four of the eight OH groups of sucrose are etherified by a 1- or 3-octyl group. The term sucrose penta-octyl ether includes any and all of the possible isomers wherein five of the eight OH groups of sucrose are etherified by a 1- or 3-octyl group. The term sucrose hexa-octyl ether includes any and all of the possible isomers wherein six of the eight OH groups of sucrose are etherified by a 1- or 3-octyl group. The term sucrose hepta-octyl ether includes any and all of the possible isomers wherein seven of the eight OH groups of sucrose are etherified by a 1- or 3-octyl group. The term sucrose octa-octyl ether means that compound wherein all eight of the OH groups of sucrose are etherified by a 1- or 3-octyl group. The composition which comprises sucrose, sucrose mono-octyl ether, sucrose di-octyl ether, sucrose tri-octyl ether, sucrose tetra-octyl ether, sucrose penta-octyl ether, sucrose hexa-octyl ether, sucrose hepta-octyl ether, and sucrose octa-octyl ether includes any combination of the sucrose ethers defined above as well as any and all of the possible isomers wherein one of the eight OH groups of sucrose is etherified by a 1- or 3-octyl group. The preferred amounts of the individual octyl ethers in the composition are from about 0% to about 20% of sucrose; from about 0% to about 20% sucrose mono-octyl ether; from about 0% to about 20% sucrose di-octyl ether; from about 0% to about 40% sucrose tri-octyl ether; from about 4% to about 50% sucrose tetra-octyl ether; from about 4% to about 60% sucrose penta-octyl ether; from about 0% to about 50% sucrose hexa-octyl ether; from about 0% to about 30% sucrose hepta-octyl ether; from about 0% to about 20% sucrose octa-octyl ether. A particularly preferred embodiment is a composition comprised of sucrose tetra-octyl ether and sucrose penta-octyl ether.

The sucrose octyl ethers according to the invention can be made by any etherification method known to those skilled in the art such as reaction of a 1-octyl halide with a mono- or poly alkoxide salt of sucrose. The preferred method comprises preparing the octadienyl ethers of sucrose by the method disclosed in co-pending patent application Ser. No. 07/517,990 filed on May 2, 1990 and then saturating them with hydrogen.

Another group of compounds according to the invention are octadienyl derivatives of substituted 2,2,6,6-tetramethylpiperidines of the formula III or IV useful as U.V. stabilizers

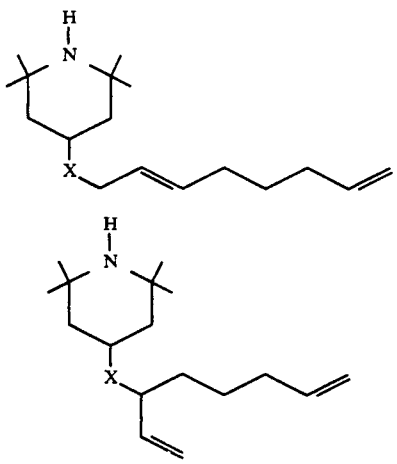

III

IV wherein X is O, NH, COO, S. The preferred method of making the compounds of formulas III and IV is by reacting 1,3-butadiene with a 2,2,6,6-tetramethylpiperidine substituted in the 4-position by a OH, $NH_2$, COOH, or SH group in the presence of a palladium (II) 2,4-pentanedionate $(Pd(acac)_2)$ triphenylphosphine catalyst in an isopropanol-water solvent mixture at about 70° C. for about 12 hours.

Another group of compounds according to the invention are those contained in a composition which is comprised of a mixture of compounds of the formula VI, VII, VIII, IX, X, and XI

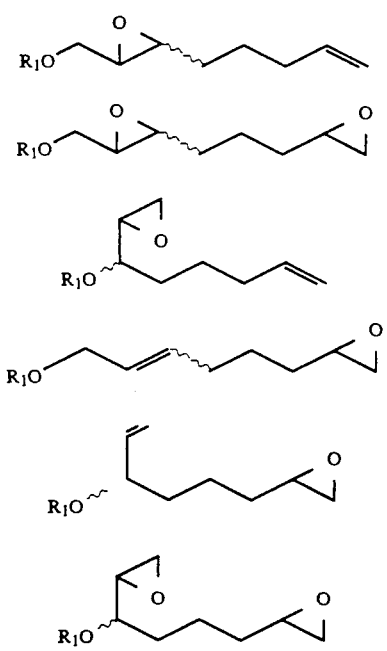

wherein $R_1$ is a $C_{1-25}$alkyl radical; a benzenoid aromatic or substituted benzenoid aromatic or an aliphatic or benzenoid aromatic acyl radical. The compounds of the formula VI-XI can be made by any method known to those skilled in the art such as by dehydrohalogention of the corresponding halohydrins or by epoxidation of the corresponding 1,7- and 2,7-octadienyl ethers with standard epoxidizing agent known to those skilled in the art. The preferred epoxidizing agents are performic acid generated in-situ and 40% peracetic acid in acetic acid.

The most preferred epoxidizing agent is performic acid generated in-situ by reacting 88% aqueous formic acid and 70% aqueous hydrogen peroxide. While the process can be carried out at any convenient temperature, the preferred temperature is about 40° C.

An additional aspect of the present invention relates to the product formed by the process comprising reacting a composition comprising a mixture of compounds of the formula VI, VII, VIII, IX, X, and XI

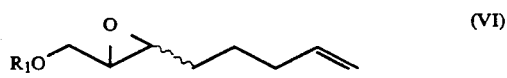

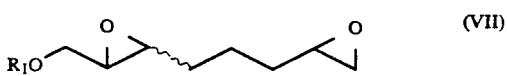

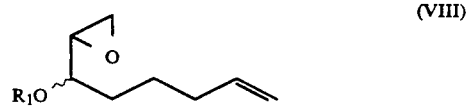

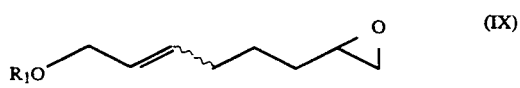

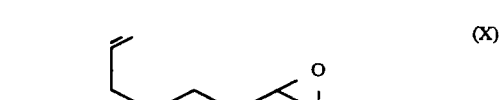

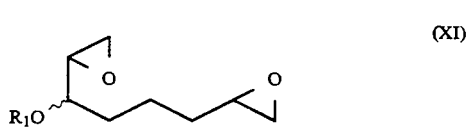

wherein $R_1$ is a $C_{1-25}$alkyl radical; a benzenoid aromatic or substituted benzenoid aromatic radical; or an aliphatic or benzenoid aromatic acyl radical with a compound selected from the group consisting of an aliphatic or aromatic alcohol, a primary aliphatic or aromatic amine, a secondary aliphatic or aromatic amine, HF, HCl, HBr, HI, water, HCN, $NaHSO_3$, and a Grignard reagent.

The starting mixture of epoxidized compounds can be made as described above. Such a mixture of epoxidized compounds can be reacted with any compound which is known to those skilled in the art as a compound which reacts with an epoxide under either acid or basic conditions to effectively open the epoxide ring and provide the corresponding alcohol derivative. For example, it is well known in the art that epoxides react with: mono functional alcohols to give ether-alcohols, with water to give diols, with aliphatic amines to give alkanolamines, with hydrogen halides to give halohydrins, with hydrogen cyanide (HCN) to give hydroxy-nitriles, with sodium bisulfite to give hydroxy-sulfonates, and with Grignard reagents to give alcohols. The process used to make composition resulting from the reaction of a mixture of compounds of the formula VI, VII, VIII, IX, X, XI, and a compound such as those disclosed above can be carried out by standard methods known to those skilled in the art. Preferably, the mixture of compounds of the formula VI, VII, VIII, IX, X, and XI is dissolved in the compound to be reacted with the mixture such as an alcohol. This reaction mixture is then heated to a temperature of from about 75° C. to about 100° C. for about 2-4 hours. The reaction mixture is then quenched with aqueous sodium bicarbonate solution and the product isolated by standard separation methods such as by removal of the starting materials and water by distillation for example.

The present invention also relates to the product formed by the process of reacting a sugar acid of the formula V

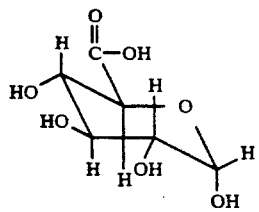

(V)

with 1,3-butadiene in the presence of a palladium (II) catalyst at a temperature of less than about 90° C. The product formed by the above process is comprised of a mixture of all possible stereo isomers and structural isomers of 1- and 3-substituted octadienyl esters and ethers of a sugar acid of the formula V. For example, GLC analysis (area %) shows that the product of the reaction of 1,3-butadiene and glucuronic acid (GA) contains dioctadienylether (12), glucuronolactone (5), glucuronic acid (22), (butenyl)ester/ether of GA (35), (octadienyl)ester/ether of GA (23), and (dioctadienyl-)ester/ether of GA (3). The composition of the reaction product will vary depending upon the nature of the sugar acid and the diene. It is preferred that the process be carried out using a Pd(acac)$_2$/tris(o-tolyl)phosphite catalyst (½ mole ratio) in an isopropanol/water (8/1 weight ratio) at 70° C. for 12 hours.

The present invention further relates to a process for telomerizing 1,3-butadiene with a carboxylic acid which comprises reacting 1,3-butadiene and a carboxylic acid in the presence of a catalyst effective amount of a palladium (II)/tris-(aryl)phosphite catalyst in the presence of a secondary or tertiary alcohol. It has been found that high yields of 1- and 3-substituted octadienyl esters can be obtained using commercially acceptable levels of palladium(II) by reacting 1,3-butadiene with a carboxylic acid using a palladium (II)/tris-(aryl)phosphite catalyst in an alcohol solvent. The preferred palladium(II) catalyst is palladium (II) acetylacetonate and the preferred tris-(aryl) phosphite is tris-(o-tolyl)-phosphite. The preferred alcohol solvents are t-butyl alcohol and isopropyl alcohol. A catalyst effective amount of a palladium (II) catalyst will range from a catalyst/ligand/carboxylic acid/butadiene molar ratio of from about 1/2/2000/5000 to about 1/2/5000/11,000. The preferred ratio is 1/2/5000/11,000. The preferred reaction temperature is 70° C.

A further aspect of the invention relates to a process for the telomerization of 1,3-butadiene with bisphenol A. The process is carried out by reacting 1,3-butadiene with bisphenol A in the presence of a palladium (II) catalyst at a temperature of from about 70° C. to about 100° C. for a period of time from about 2 hours to about 12 hours wherein the palladium (II)/bisphenol A/diene molar ratio is from about 1/2500/4800 to about 1/60,000/300,000. The preferred palladium (II) catalyst is palladium (II) 2,4-pentanedionate/triphenylphosphine (½ mole ratio). The preferred palladium (II)/bisphenol A/diene molar ratio is 1/10,000/50,000. The preferred reaction temperature is 75° C.

The following examples are meant to illustrate but not limit the invention.

EXAMPLE 1

Preparation of Sucrose Octyl Ethers (N=4.0)

A one gallon autoclave was charged with palladium (II) 2,4-pentanedionate (0.7416 g, 2.43 mmol), triphenylphosphine (1.275 g, 4.96 mmol), isopropanol (1178 g, 19.6 mol), water (150 g, 8.3 mol), and sucrose (1000 g, 2.92 mol). While stirring at 600 rpm, the reactor was subjected to three evacuation/purge with nitrogen cycles after which, 1,3-butadiene (853 g, 15.8 mol) was added. The contents were heated to 65° C. for five hours, after which they were allowed to cool to room temperature and the unreacted butadiene (<10% of charge) was vented carefully. 2.4 kg of a light yellow/green, clear solution is obtained after filtration to remove residual solid sucrose (530 g).

The solution was then combined with 50 g of active Raney Nickel catalyst in a one gallon high pressure autoclave. While agitating at 500 rpm, the solution was subjected to three purge cycles in which the vessel was evacuated and then hydrogen was added to 50 psi. After the last purge, the solution was warmed to 100° C. and maintained at 1100 psi of hydrogen pressure for 12 hours. After cooling and venting, the solution was filtered to remove Raney Nickel and then rotovapped to remove 90% of the volatiles (solvent and side products) yielding a hazy solution. The material was clarified by pressure filtration and then subjected to steam enhanced wiped film evaporation for complete removal of volatiles. The resultant material (750 g) had the following characteristics: Iodine value=2.4; hydroxyl value=288; average degree of substitution (N)=4.0 (as determined by PMR); Pd=<1.8 ppm; Ni=5.1 ppm. HPLC product distribution (area %); sucrose (0.22); monoethers (0.83); diethers (8.06) triethers (19.04); tetraethers (30.75); pentaethers (28.71); hexaethers (11.88); heptaethers (0.51); octaethers (0.00).

EXAMPLE 2

Preparation of Sucrose Octyl Ethers (N=5.5)

A one gallon autoclave was charged with palladium (II) 2,4-pentanedionate (0.7550 g, 2.48 mmol), triphenylphosphine (1.302 g, 4.96 mmol), isopropanol (820 g, 13.64 mol), water (110 g, 6.11 mol), and sucrose (510 g, 1.488 mol). While stirring at 600 rpm, the reactor was subjected to three evacuation/purge with nitrogen cycles after which, 1,3-butadiene (1340 g, 24.81 mol) was added. The contents were heated to 65° C. for ten hours, after which they were allowed to cool to room temperature and the unreacted butadiene (<15% of charge) was vented carefully. 2.5 kg of a light yellow/green, clear solution was obtained after filtration to remove residual solid sucrose (20 g).

The solution was then combined with 50 g of active Raney Nickel catalyst in a one gallon high pressure autoclave. While agitating at 500 rpm, the solution was subjected to three purge cycles in which the vessel was evacuated and then hydrogen was added to 50 psi. After the last purge, the solution was warmed to 100° C. and maintained at 1000 psi of hydrogen pressure for 24 hours. After cooling and venting, the solution was filtered to remove the Raney Nickel then rotovapped to remove 90% of the volatiles (solvent and side products). The material was then subjected to steam enhanced wiped film evaporation for complete removal of volatiles. The resultant material (1.1 kg) had the following characteristics: Iodine value=11.5; hydroxyl value=170; average degree of substitution (N)=5.7 (as determined by PMR); Pd=<1.8 ppm; Ni=1.8 ppm. HPLC product distribution (area %); sucrose (0.01); monoethers (0.00); diethers (0.16); triethers (1.82); tetraethers (15.09); pentaethers (32.53); hexaethers (36.05); heptaethers (13.99); octaethers (0.34).

EXAMPLE 3

Preparation of Glucose Octyl Ethers (N=2)

A one gallon autoclave was charged with palladium (II) 2,4-pentanedionate (0.8685 g, 2.85 mmol), triphenylphosphine (1.495 g, 5.70 mmol), isopropanol (820 g, 13.64 mol), water (110 g, 6.11 mol), and anhydrous glucose (513 g, 2.85 mol). While stirring at 600 rpm, the reactor was subjected to three evacuation/purge with nitrogen cycles after which, 1,3-butadiene (1124 g, 20.81 mol) was added. The contents were heated to 65° C. for twelve hours, after which they were allowed to cool to room temperature and the unreacted butadiene (<10% of charge) was vented carefully. 2.4 kg of a light yellow/green, clear solution was obtained after filtration to remove residual solid glucose (40 g). 500 g of the filtrate was combined with 12 g of active Raney Nickel catalyst in a one liter, high pressure autoclave. While agitating at 500 rpm, the solution was subjected to three purge cycles in which the vessel was evacuated and then hydrogen added to 50 psi. After the last purge, the solution was warmed to 85° C. and maintained at 1000 psi of hydrogen for four hours. After cooling and venting, the solution was filtered to remove the Raney Nickel and then rotovapped to remove 90% of the volatiles (solvent and side products) yielding a hazy solution. The material was clarified by pressure filtration and then subjected to steam enhanced wiped film evaporation for complete removal of volatiles. The resultant material (240 g) had the following characteristics: Iodine value=0.9; hydroxyl value=344; average degree of substitution (N)=2.0; Pd= <1.8 ppm; Ni=14 ppm; glucose=0.3 wt %. GLC analysis (area %); glucose (1.3); monoethers (13.6); diethers (37.44); triethers (39.62); tetraethers (7.8); pentaethers (not detectable by GLC). GLC results based on trimethylsilane derivatized products under the following conditions; Supelco SPB-5 column; temperature program from 200° to 320° C. at 10° C./minute.

EXAMPLE 4

Epoxidation of the Octadienyl Ethers of a $C_{12}$Alcohol

A 100 mL one-neck, round-bottomed flask containing a magnetic stir bar was charged with a mixture of the octadienyl ethers of commercial dodecanol (2.95 g, 0.010 mole), 88% aqueous formic acid (0.2 mL) and 70% aqueous hydrogen peroxide (1.0 mL). The mixture was stirred vigorously and heated to 40° C. At hourly intervals the reaction was recharged with fresh peroxide (1.0 mL) and at bi-hourly intervals formic acid (0.2 mL) was added to maintain a constant concentration of acid in the aqueous phase. Small samples (10 microL) were removed periodically to check the extent of epoxidation. The reaction was continued in the stated manner until the starting telomer diene level had fallen to 1-2% of the total mixture. Alternatively, the reaction may be left stirring at ambient temperature overnight and the stated addition scheme restarted (after warming the mixture to 40° C.) the next day. The residual acid was quenched with saturated aqueous sodium bicarbonate solution and stirring was continued for an additional three hour period while residual peroxide decomposed. The reaction mixture was poured into 50 mL of ether in a separatory funnel and the product epoxides were partitioned between the organic and aqueous phases. The aqueous phase was discarded and the organic phase was washed with 10 mL of water then dried over anhydrous magnesium sulfate. After filtration and concentration of the filtrate, further drying was completed by stripping the material overnight at reduced pressure (approx. 0.1 torr) and 30° C. Yield: 3.4 g.

EXAMPLE 5

Preparation of the Octadienyl Ethers of 4-hydroxy-2,2,6,6-tetramethylpiperidine

A 100 mL capacity two-port glass autoclave containing a magnetic stir bar and fitted with a pressure gauge and cap was charged with Pd(acac)$_2$(6.1 mg, 20 μmol), triphenylphosphine (10.5 mg, 40 μmol), 4-hydroxy-2,2,6,6-tetramethylpiperidine (1.57 g, 10.0 mmol) and isopropyl alcohol solvent (5.0 mL). The apparatus was cooled below ambient temperature and the air in the autoclave was replaced with nitrogen by means of two pump/purge cycles (evacuation of the reactor to ≈0.2 torr and refilling with N$_2$ to ambient pressure) while the reactants were mixed by stirring. Butadiene (2.7 g, 50 mmol) was introduced into the autoclave via syringe while N$_2$ was swept over the top of the reactants and out the uncapped opening. The autoclave was then sealed and the mixture was allowed to warm to ambient temperature before being placed in an oil bath heated to 70° C. The reaction mixture was stirred at this temperature for a period of 12 hours. Unreacted butadiene was vented and GC analysis of the resulting mixture showed unreacted piperidine, octadienyl ethers III and IV (X=O) and a small amount of a butadiene vinyl ether.

EXAMPLE 6

Telomerization of 1,3-Butadiene with Glucuronic Acid

To a 125 ml stainless steel Parr bomb equipped with magnetic stir bar, was added Pd(acac)$_2$ (0.0153 g, 0.05 mmol), tris(2-tolyl)phosphite (0.0352 g, 0.10 mmol), glucuronic acid (GA)(4.85 g, 25 mmol), isopropanol (7.85 g, 10 ml), and water (1.0 g, 1.0 ml). The reactor top (complete with inlet/outlet valves and pressure gauge) was then sealed and the assembly weighed. While cooling in a dry ice bath, the reactor was evacuated and flushed with argon three times. Butadiene (7.7 g, 143 mmol) was added and then all valves were closed. The assembly was then reweighed to accurately determine the amount of butadiene added. The autoclave was then warmed to 70° C. for 12 hours while stirring at 500 rpm. After cooling to room temperature, the reactor was weighed to verify no loss by leakage. Remaining butadiene was vented and then the assembly was weighed again and diene conversion was determined to be 92%. The cloudy solution was filtered and the resultant filtrate rotovapped yielding 6.3 g of yellow product mixture. GLC analysis (area %) shows dioctadienylether (12), glucuronolactone (5), glucuronic acid (22), (butenyl)ester/ether of GA (35), (octadienyl)ester/ether of GA (23), and (dioctadienyl)ester/ether of GA (3). Component masses were verified by GC/MS.

EXAMPLE 7

Preparation of Ring-Opened Derivatives of Epoxidized Telomer Products

The telomer epoxide mixture from Example 4 (3.4 g) was dissolved in 15 mL of absolute methanol. One drop of concentrated sulfuric acid was added and the mixture was stirred at ambient temperature for a period of 5 h. The reaction was quenched with 10 drops of saturated $NaHCO_3$. Excess methanol was removed with a rotary evaporator. The concentrate was diluted with ether and filtered through celite. The filtrate was concentrated as before to afford 3.5 g; GC/MS analysis confirmed the presence of the methoxy-alcohol functionality.

EXAMPLE 8

Preparation of Bisphenol A Dioctadienyl Ethers (2,2-bis[4-(2,7-octadienyloxy)phenyl]propane)

A one gallon autoclave was charged with palladium (II) 2,4-pentanedionate (0.150 g, $4.92 \times 10^{-4}$ mol), triphenylphosphine (0.255 g, $9.72 \times 10^{-4}$ mol) and bisphenol A (1125 g, 4.92 mol). While stirring at 600 RPM, the reactor was subjected to three evacuation/purge with nitrogen cycles after which, 1,3-butadiene (1328 g, 22.6 mol) was added. The contents were heated to 75° C. for two hours, after which they were allowed to cool to room temperature and the unreacted butadiene (<10% of charge) was vented carefully. The clear reaction mixture (2.23 kg) was drained and then subjected to steam enhanced wiped film evaporation, yielding 2.0 kg of nearly colorless, odorless, bisphenol A dioctadienyl ethers (>96% pure) with the following characteristics: Iodine value=224; hydroxyl value=<1.

EXAMPLE 9

Telomerization of Butadiene with Octanoic Acid in Isopropanol

A 125-mL, 2-necked glass autoclave, fitted with a pressure gauge, inlet valve and cap, was charged with $Pd(acac)_2$(2.4 mg, 8 μmol), tris(o-tolyl)phosphine (5.6 mg, 16 μmol), isopropyl alcohol solvent (10 mL) and octanoic acid (3.6 g, 25 mmol). The apparatus was cooled to −70° C. in a dry ice/acetone bath. The air in the autoclave was removed under vacuum and replaced with nitrogen. Butadiene (3.8 g, approx. 5 mL, 59 mmol) was added to the reaction mixture with a syringe while the apparatus was purged with nitrogen. The autoclave was sealed and the contents were allowed to warm to ambient temperature. The reaction mixture was heated in an oil bath for a period of 12 h at 50° C. After allowing the mixture to cool to ambient temperature, excess butadiene was carefully vented from the autoclave. The apparatus was weighed to determine the amount of butadiene that underwent reaction. Butadiene conversion was 79% by difference. After removal of the solvent by rotary evaporation, the yield of telomer products was found to be 6.9 g. Analysis of the product mixture by capillary GC showed that it consisted of 93% octadienyl esters of octanoic acid. This represents a near quantitative conversion of octanoic acid to C8 telomer products.

EXAMPLE 10

Telomerization of Butadiene with Octanoic Acid in Isopropanol

A 125-mL, stainless steel autoclave, fitted with a pressure gauge, inlet valve and rupture disk assembly, was charged with $Pd(acac)_2$(3.0 mg, 10 μmol), tris(o-tolyl)phosphine (7.0 mg, 20 μmol), isopropyl alcohol solvent (10 mL) and octanoic acid (7.1 g, 50 mmol). The apparatus was cooled to −70° C. in a dry ice/acetone bath. The air in the autoclave was removed under vacuum and replaced with nitrogen. Butadiene (7.2 g, approx. 9 mL, 112 mmol) was added to the reaction mixture with a syringe while the apparatus was purged with nitrogen. The autoclave was sealed and the contents were allowed to warm to ambient temperature. The reaction mixture was heated in an oil bath for a period of 12 h at 110° C. After allowing the mixture to cool to ambient temperature, excess butadiene was carefully vented from the autoclave. The apparatus was weighed to determine the amount of butadiene that underwent reaction. Butadiene conversion was 90% by difference. After removal of the solvent by rotary evaporation, the yield of telomer products was found to be 13.5 g. Analysis of the product mixture by capillary GC showed that it consisted of 87% octadienyl esters and 7% residual octanoic acid.

What is claimed is:

1. A process for telomerizing 1,3-butadiene with a carboxylic acid which comprises reacting 1,3-butadiene and a carboxylic acid in the presence of a catalyst effective amount of a palladium (II)/tris-(aryl)phosphite catalyst in the presence of a secondary or tertiary alcohol.

2. The process of claim 1, wherein said secondary alcohol is isopropanol.

3. The process of claim 1, wherein said palladium (II)/tris-(aryl)phosphite catalyst is palladium (II) acetylacetonate/tris-(aryl) phosphite.

4. The process of claim 1, wherein the tris-(aryl) phosphite is tris-(o-tolyl) phosphite.

5. The process of claim 3 wherein the tris-(aryl) phosphite is tris-(o-tolyl) phosphite.

6. The process of claim 1, wherein the molar ratio of palladium (II)/tris-(aryl) phosphite/carboxylic acid/1, 3-butadiene is in the range of from about 1/2/2000/5000 to about 1/2/5000/11,000.

7. The process of claim 1 wherein the palladium (II)/-tris-(aryl) phosphite catalyst is palladium (II) acetylacetonate/tris-(aryl) phosphite, and wherein the molar ratio of palladium (II)/tris-(aryl) phosphite/carboxylic acid/1, 3-butadiene is in the range of from about 1/2/2000/5000 to about 1/2/5000/11,000.

8. The process of claim 7 wherein the tris-(aryl) phosphite is tris-(o-tolyl) phosphite.

9. The process of claim 7 wherein the alcohol is t-butyl alcohol or isopropyl alcohol.

* * * * *